United States Patent
McIntyre

(10) Patent No.: US 10,809,272 B2
(45) Date of Patent: Oct. 20, 2020

(54) BIOMARKERS, KITS, AND METHOD FOR DIAGNOSING, MONITORING, AND/OR STAGING ALZHEIMER'S DISEASE

(75) Inventor: John A. McIntyre, Indianapolis, IN (US)

(73) Assignee: REDOX-REACTIVE REAGENTS, LLC, Beech Grove, IN (US)

(*) Notice: Subject to any disclaimer, the term of this patent is extended or adjusted under 35 U.S.C. 154(b) by 1563 days.

(21) Appl. No.: 12/554,497

(22) Filed: Sep. 4, 2009

(65) Prior Publication Data

US 2010/0062457 A1    Mar. 11, 2010

Related U.S. Application Data

(60) Provisional application No. 61/094,167, filed on Sep. 4, 2008.

(51) Int. Cl.
*G01N 33/68* (2006.01)

(52) U.S. Cl.
CPC . *G01N 33/6896* (2013.01); *G01N 2800/2821* (2013.01)

(58) Field of Classification Search
CPC ........... G01N 27/3277; G01N 33/6854; G01N 2800/2821; G01N 33/6896
See application file for complete search history.

(56) References Cited

U.S. PATENT DOCUMENTS

2005/0260681 A1   11/2005   McIntyre
2006/0141541 A1    6/2006   McIntyre

FOREIGN PATENT DOCUMENTS

WO    WO2007/106224      9/2007

OTHER PUBLICATIONS

Irizari. Biomarkers of Alzheimer Disease in Plasma. NeuroRx. Apr. 2004; 1(2): 226-234.*
International Search Report and Written Opinion; International application No. PCT/US2009/056044; International Filing Date: Sep. 4, 2009.
JP Office Action of Appln. No. 2011-526230 dated Apr. 24, 2012 with English translation.

* cited by examiner

*Primary Examiner* — Gregory S Emch
(74) *Attorney, Agent, or Firm* — Fitch, Even, Tabin & Flannery, LLP

(57) ABSTRACT

The present invention is directed to a biomarker and kit for diagnosing, monitoring and/or staging Alzheimer's disease comprising redox-reactive autoantibodies. The present invention is also directed to a method for diagnosing, monitoring and/or staging Alzheimer's disease which comprises conducting a blood test using the same.

13 Claims, 2 Drawing Sheets

Classification and Regression Tree (CART) Analysis

Specificity = 14/14 = 1.00 = 100%
Sensitivity = 16/19 = .842 = 84%

AD:

NORMAL.

BIOMARKERS, KITS, AND METHOD FOR DIAGNOSING, MONITORING, AND/OR STAGING ALZHEIMER'S DISEASE

CROSS-REFERENCE TO RELATED APPLICATIONS

This application claims the benefit of the filing date of provisional application Ser. No. 61/094,167, filed on Sep. 4, 2008. This provisional application is incorporated herein by reference.

FIELD OF THE INVENTION

The present invention relates to a method for diagnosing, monitoring and/or staging Alzheimer's disease, including a blood test for redox-reactive autoantibodies. In addition, the present invention also relates to a biomarker and a kit for diagnosing, monitoring and/or staging Alzheimer's disease.

BACKGROUND

In all but specialized Alzheimer's Research Centers, the diagnosis of Alzheimer's disease (AD) largely involves an exclusive approach of secondary causes and other forms of dementia. Oral testing of a patient's cognitive/memory abilities is commonly used for assessments, via the Alzheimer's disease Assessment Scale-cognition (ADAS-cog) measure (Pena-Casanova. Alzheimer's disease assessment scale-cognitive in clinical practice. Int Psychogeriatr 1997; 9:105-114), and the Mini-Mental State Examination (MMSE) (Tombaugh T N, McIntyre N J. The mini-mental state examination: A comprehensive review. J Am Geriatr Soc 1992; 40:922-935). However, these tests contain sections that are unavoidably subjective, and when used, can only be administered and scored by qualified health care professionals, including, for example, psychologists, physicians, and nurses. Unfortunately, most front line primary care physicians do not have time to perform these tests. Alternatively, a blood test can also be used to discriminate Alzheimer's disease (AD) from other forms of dementia.

Even for specialized Alzheimer's Research Centers, only a few centers have access to sophisticated and time consuming tests and specifically trained professionals who can properly diagnose Alzheimer's disease (AD) based on medical history, pattern of cognition defects (for example, the history of how they developed), short-term memory problems, word finding and judgment. Using these parameters, diagnosis of AD meets and/or exceeds 98% sensitivity and 88% specificity (Lopez O L, Becker J T, Klunk W, Saxton, Hamilton R L, Kaufer D I, Sweet R A, Meltzer C C, Wisniewski S, Kamboh M I, DeKosky S T. Research evaluation and diagnosis of probable Alzheimer's disease over the last two decades: I. 2000; 55:1854-1862). These evaluations have been further expanded and clarified by taking into consideration co-morbid conditions that also can affect cognition (Lopez O L, Becker J T, Klunk W, Saxton, Hamilton R L, Kaufer D I, Sweet R A, Meltzer C C, Wisniewski S, Kamboh M I, DeKosky S T. Research evaluation and diagnosis of probable Alzheimer's disease over the last two decades: II. 2000; 55:1863-1869).

Hence, the need for better AD biomarkers is paramount. According to the 1998 Consensus report of the working group on molecular and biochemical markers of Alzheimer's disease, an ideal biomarker should have a greater than 80% sensitivity and specificity for excluding other forms of dementia and neurodegenerative processes. In addition, the ideal biomarker should be reliable, reproducible, and non-invasive, easy to perform, and inexpensive (Consensus report of the working group on molecular and biochemical markers of Alzheimer's disease. The Ronald and Nancy Reagan Research institute of Alzheimer's Association and the National Institute on Aging Working Group. Neurobiol Aging 1998; 19:109-116).

To date, three candidate biomarkers have been suggested to approximate these requirements, albeit, the non-invasive prerequisite not withstanding. These biomarkers are found in the cerebrospinal fluid (CSF) and are: total tau protein, amyloid-β protein (A $β_{42}$) and phosphorylated tau protein (Formichi P, Bartisti C, Radi E, Federico A. Cerebrospinal fluid tau A β, and phosphorylated tau protein for the diagnosis of Alzheimer's disease. J Cell Physiol 2006; 208:39-46).

Recent evaluation of a new kit assay designed to measure levels of various forms of Aβ protein in blood for possible use in early detection of Alzheimer's disease was made available for research since the summer of 2007 (INNO-BIA plasma Aβ forms, Innogenetics, Gent Belgium). This test establishes an $Aβ_{42}/Aβ_{40}$ ratio that is lower in patients with a predisposition for developing mild cognitive impairment (MCI), which usually precedes Alzheimer's disease. This observation relates to findings in both human and mouse models that show decrease CSF and plasma $Aβ_{42}$ levels as $Aβ_{42}$ aggregates and deposits in the brain (Graff-Radford NR, Crook J E, Lucas J, Boeve B F, Knopman D S, Lvnik R J, Smith G E, Younkin L H, Petersen R C, Younkin S G. Association of low plasma Abeta42/Abeta40 ratios with increase imminent risk for mild cognitive impairment and Alzheimer's disease. Arch Neurol 2007; 64:3543-362). Unfortunately, peripheral Aβ measurements are subject to conflicting reports due to the confounding existence of serum lipoproteins, Fc-binding proteins and the low concentrations of Aβ in the serum (Kawarabayashi T, Shoji M. Plasma biomarkers of Alzheimer's disease. Curr Opin Psych 2008; 21:260-267). Furthermore, Aβ serum levels are affected by renal function (Bailey P. Biological markers in Alzheimer's disease. Can J Neurol Sci 2007; 34:S72-S76; and Dubois B, Feldman H H, Jacova C, Dekosky S T, BarbergerGateau P, Cummings J, Delacourte A, Galasko D, Gauthier S, Jicha G, Meguro K, O'Brien J, Pasquier F, Robert P, Rossor M, Saloway S, Stern Y, Visser P J, Scheltens P. Research criteria for the diagnosis of Alzheimer's disease: Revising the NINCDS-ADRDA criteria. Lancet Neurol 2007; 6:734-746) and medications (Jellinger K A, Janetzky B, Attems J, Kienzl E. Biomarkers for early diagnosis of Alzheimer's disease: 'ALZheimer's ASsociated gene'—a new blood biomarker. J Cell Mol Med 2008; 12:1094-1117). In short, the future for plasma Aβ testing as a primary biomarker is questionable.

A complex blood plasma molecular test for diagnosis of Alzheimer's disease is described by Ray et al. (Ray et al. Classification and prediction of clinical Alzheimer's diagnosis based on plasma signaling proteins. Nature Med 2007; 11:1359-1362), wherein 18 out of 120 signaling proteins were found with 90% accuracy to be predictive "markers" of Alzheimer's disease. However, the statistical interpretations of these 18 signaling protein microarray proteins are cumbersome and cannot be readily converted into an easy and inexpensive test. These 18 identified markers also implicate an involvement of the immune response.

Hence, there is a need for universal accepted biomarkers for diagnosing, monitoring and/or staging neurodegenerative diseases such as Alzheimer's disease that are fast, more accurate, and less expensive.

The present inventor has found an Alzheimer's disease biomarker test that will have a highly positive impact on services and treatments that drive this field. Alzheimer's disease (AD) is a progressive brain disorder that gradually destroys a person's memory and ability to learn, reason, make judgments, communicate and carry out daily activities. As AD progresses, individuals may also experience changes in personality and behavior, such as anxiety, suspiciousness or agitation, as well as delusions or hallucinations. AD advances at widely different rates. People with AD die an average of four to six years after diagnosis, but the duration of the disease can vary from three to 20 years. Furthermore, AD is a disease that is rapidly affecting more people in this country. There are now more than 5 million people in the United States living with Alzheimer's disease. This number includes 4.9 million people over the age of 65 and between 200,000 and 500,000 people under age 65 with early-onset AD and other dementias. It is estimated that only 20%-40% of people with AD have been diagnosed, leaving an undiagnosed population of 12.5 MM to 25 MM people. Additionally, approximately 500,000 Americans per year are expected to develop AD, increasing to over 1,000,000 Americans per year by 2050.

Given the increasing numbers of people affected by AD, there is great need for a diagnostic biomarker for the disease, especially due to the fact that there is no single test that proves a person has Alzheimer's disease prior to the present invention. Experts estimate a skilled physician can now diagnose AD with more than 90 percent accuracy, although there is no certainty until a post-mortem autopsy is conducted. Monitoring of disease progression is mainly focused on measuring cognitive decline. The underlying state of the disease is left unmonitored because there is currently no viable mechanism for doing so prior to the present invention.

Since Alzheimer's disease is incurable, there is a great need for a diagnosis that is inexpensive, quick, and accurate.

SUMMARY OF THE INVENTION

Various aspects and example embodiments of the present invention relate to redox-reactive antiphospholipid antibodies used as biomarkers for diagnosing, monitoring and/or staging neurodegenerative diseases or neurological disorders such as Alzheimer's disease. Neurodegenerative diseases or neurological disorders, such as Alzheimer's disease can be diagnosed by conducting a blood test for redox-reactive autoantibodies (R-RAA) that is fast, less expensive and more accurate than available diagnostic tools.

The present invention relates to a method for diagnosing, monitoring and/or staging Alzheimer's disease which comprises conducting a blood test for redox-reactive autoantibodies. The autoantibodies are at least one of IgG, IgM, IgA, IgE, and IgD. The autoantibodies can also be autoantibodies which bind to phospholipids, wherein the phospholipids are at least one of phosphatidylserine, cardiolipin, phosphatidylethanolamine and phosphatidylcholine.

The method of the present invention also comprises an assay that can detect antiphospholipid autoantibodies. The assay can be any assay known in the art that can detect antiphospholipid autoantibodies including, but not limited to, immunoassays. Some examples of an immunoassay can include, but not limited to radio immunoassay (RIA), enzyme immunoassay (EIA), flow cytometry, and Western blot. The autoantibodies that the assay of the present invention can detect include at least one of IgG, IgM, IgA, IgE, and IgD. The autoantibodies that the assay of the present invention can detect can bind to at least one phospholipid. The phospholipids can be, but not limited to, phosphatidylserine, cardiolipin, phosphatidylethanolamine and phosphatidylcholine.

The present invention also relates to a biomarker for diagnosing, monitoring and/or staging Alzheimer's disease which comprises redox-reactive autoantibodies. The autoantibodies are at least one of IgG, IgM, IgA, IgE, and IgD. The autoantibodies are autoantibodies which bind to phospholipids. The phospholipids can be, but not limited to, at least one of phosphatidylserine, cardiolipin, phosphatidylethanolamine and phosphatidylcholine.

In addition, the present invention relates to a kit for diagnosing, monitoring and/or staging Alzheimer's disease which comprises an assay which can detect antiphospholipid autoantibodies. The autoantibodies are at least one of IgG, IgM, IgA, IgE, and IgD. The autoantibodies are autoantibodies which bind to phospholipids. The phospholipids can be, but not limited to, at least one of phosphatidylserine, cardiolipin, phosphatidylethanolamine and phosphatidylcholine. The assay can be any assay known in the art that can detect antiphospholipid autoantibodies including, but not limited to, immunoassays. Some examples of an immunoassay can include, but not limited to radio immunoassay (RIA), enzyme immunoassay (EIA), flow cytometry, and Western blot. The autoantibodies that the assay of the present invention can detect include at least one of IgG, IgM, IgA, IgE, and IgD. The autoantibodies that the assay of the present invention can detect can bind to at least one phospholipid. The phospholipids can be, but not limited to, phosphatidylserine, cardiolipin, phosphatidylethanolamine and phosphatidylcholine.

BRIEF DESCRIPTION OF THE FIGURES

A better understanding of the present invention will become apparent from the following detailed description of example embodiments and the claims when read in connection with the accompanying drawings, all forming a part of the disclosure of this invention. While the following written and illustrated disclosure focuses on disclosing example embodiments of the invention, it should be clearly understood that the same is by way of illustration and example only and that the invention is not limited thereto. The spirit and scope of the present invention are limited only by the terms of the appended claims. The following represents brief descriptions of the drawings, wherein:

DESCRIPTION OF THE INVENTION

Figure 1:
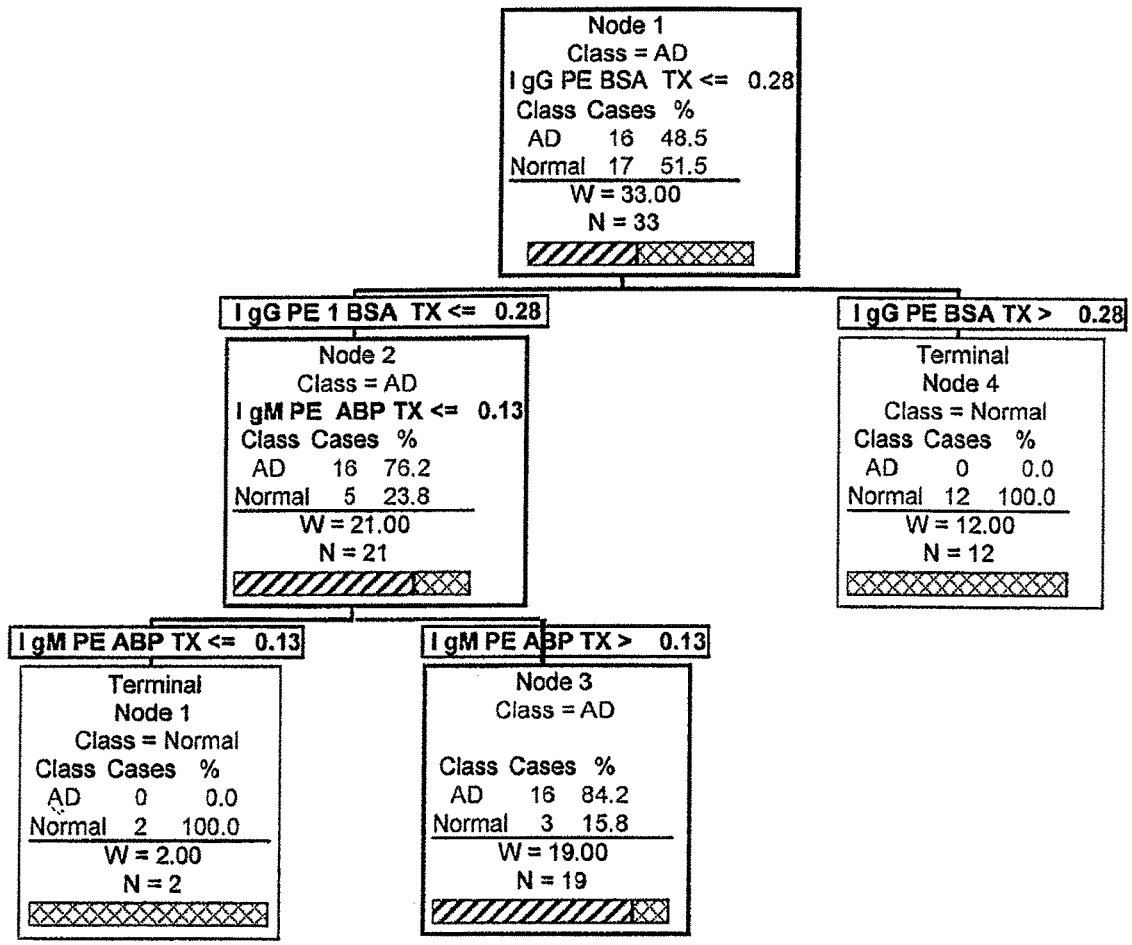
FIG. 1 shows a Classification and Regression Tree (CART) analysis illustrating the differentiation between the Alzheimer's disease serum samples versus the normal serum samples to have a sensitivity of 94% and a specificity of 100%.
Figure 1:
Figure 1:

Prior to the present invention, there is no universally accepted inclusive biomarker(s) for diagnosing, monitoring and/or staging neurodegenerative diseases such as Alzheimer's. Neurodegenerative diseases, for example, Alzheimer's, Parkinson's, ALS and multiple sclerosis are associated with increased oxidative stress in the central nervous system (CNS), which results in oxidation of proteins, lipids and DNA. Other neurological disorders including neurological disorders in patients with cerebrovascular disease is also associated with increased oxidative stress in the central nervous system (CNS), which results in oxidation of proteins, lipids and DNA.

Prior to the present invention, few studies have been published that report upon the presence of antiphospholipid (aPL) autoantibodies other than anticardiolipin (aCL) in Alzheimer's patient bloods. Also prior to the present invention, no reports are available that describe the serum presence of redox-reactive autoantibodies (R-RAA) in patients with neurodegenerative diseases compared to age-matched normal individuals.

A novel family of autoantibodies that exists in the blood is capable of recognizing autoantigen subsequent to oxidation-reduction (redox) reactions (McIntyre J A, Wagenknecht D R, Faulk W P. Autoantibodies unmasked by redox reactions. J Autoimmun 2005; 24:311-317, which is incorporated herein by reference in its entirety). Without an oxidative environment these "masked" R-RAA cannot be detected in conventional assays, thereby differentiating them from the natural and hidden autoantibodies that are known in the art (Cabiedes et al. Hidden antiphospholipid antibodies in normal human sera circulate as immune complexes whose antigen can be removed by heat, acid, hypermolar buffers or phospholipase treatments. Eur J Immunol 1998; 7:2108-2114; Lorber et al. Hidden autoantibodies. Clin Rev Allergy Immunol 2000; 1:51-58; and Tomer et al. The significance of natural autoantibodies. Immunol Invest 1988; 5:389-424.)

The present inventor noted that there is an abnormal increase of oxidative stress in the central nervous system (CNS) of Alzheimer's patients that causes oxidation of proteins, lipids and DNA. The present inventor discovered that the antiphospholipid (aPL) autoantibodies, that are members of the redox-reactive autoantibody (R-RAA) family, are significantly decreased or absent in the cerebrospinal fluids of autopsy-confirmed Alzheimer's disease patients (McIntyre J A, Chapman J, Shavit E, Hamilton R L, Dekosky S T. Redox-reactive autoantibodies in Alzheimer's patient's cerebrospinal fluids: Preliminary studies. Autoimmunity 2007; 40:390-396). Because of the known elevation of oxidation-induced damage in the CNS and the abnormal enrichment of redox reactive metals in postmortem AD brains, the present inventor discovered that the R-RAA in the blood of AD patients show a departure from the normal aPL levels.

Prior to the present invention, no studies have been published that report upon the presence of aPL other than aCL in Alzheimer's patient bloods. In addition, prior to the present invention, no reports exist that describe the presence and/or levels of R-RAA in the blood from patients with Alzheimer's disease.

The present inventor discovered that oxidation "unmasked" antibodies in the blood and other body fluids from normal, healthy individuals revealing autoantibodies that are associated with autoimmune disorders. Conversely, oxidation of autoantibodies from individuals with autoimmune diseases can also cause remasking of their autoantibodies which then become undetectable. These conversions depend upon oxidation-reduction reactions and define a new family of autoantibodies that has been designated as redox-reactive autoantibodies (R-RAA).

It is noted that R-RAA were first identified in blood, cerebrospinal fluid (CSF), and breast milk of healthy individuals tested. R-RAA of G, M, and A isotypes exist in all animals tested to date (horses, dogs, rats, mice and IgY for chickens) and are likely found in all vertebrates. Studies have shown that CSF from normal individuals is limited to IgG, whereas breast milk is primarily IgA. Blood contains all three G, M, and A isotypes. (McIntyre J A, Faulk W P. Redox-reactive autoantibodies: Biochemistry, characterization, and specificities. Clin Rev Allergy Immunol 2009; 37:49-54, which is incorporated herein by reference in its entirety).

The present inventor compared serum samples from 16 AD patients to 17 serum samples from age-matched volunteer blood bank donors. Each serum was tested before and after hemin oxidation for four antiphospholipid autoantibody (aPL) specificities by using an in-house enzyme-linked immunosorbent assay (ELISA). Comparisons between the AD and normal populations for antiphosphatidylethanolamine (aPE) activities revealed highly significant differences. Discriminate analysis between the AD and the normal serum samples showed a sensitivity of 88% and a specificity of 94%. A Classification and Regression Tree (CART) analysis revealed the differentiation between the AD versus the normal serum samples to have a sensitivity of 94% and specificity of 100%.

This study by the present inventor is the first to indicate that blood tests for R-RAA can be used as an inclusive laboratory criterion for neurological disorders diagnosis, for example Alzheimer's disease. The present inventor discovered that blood tests for R-RAA can be useful for diagnosing, monitoring and/or staging neurodegenerative diseases.

The present invention relates to redox-reactive antiphospholipid antibodies used as biomarkers for diagnosing, monitoring and/or staging neurodegenerative diseases or neurological disorders. The present invention also relates to a kit for diagnosing, monitoring and/or staging neurodegenerative diseases or neurological disorders which comprises an assay which can detect antiphospholipid autoantibodies.

The present invention is directed to a method for diagnosing, monitoring and/or staging neurological disorders comprising the steps of conducting a blood test for redox-reactive autoantibodies. The autoantibodies can be autoantibodies that bind to phospholipid. The phospholipid can be, but not limited to, phosphatidylserine, cardiolipin, phosphatidylethanolamine, and phosphatidylcholine. Neurological disorders can include all neurological disorders known in the art such as, but not limited to, Parkinson's, Alzheimer's, multiple sclerosis (MS) that are associated with increased levels of oxidative stress in the CNS. Neurological disorders can include, but not limited to, neurological disorders in patients with cerebrovascular disease. Different stages of a neurological disorder, such as Alzheimer's disease can be determined via the method of the present invention by amount of redox-reactive autoantibodies identified. In later stages, less redox-reactive autoantibodies are present. Near to an end stage, sometimes no redox-reactive autoantibodies are detectable. The present invention can also allow monitoring patients with neurological disorders.

The method of the present invention also comprises an assay that can detect antiphospholipid autoantibodies. The assay can be any assay known in the art that can detect antiphospholipid autoantibodies including, but not limited to immunoassays. Some examples of an immunoassay can include, but not limited to radio immunoassay (RIA), enzyme immunoassay (EIA), flow cytometry, and Western blot. The autoantibodies that the assay of the present invention can detect include at least one of IgG, IgM, IgA, IgE, and IgD. The autoantibodies that the assay of the present invention can detect can bind to at least one phospholipid. The phospholipids can be, but not limited to, phosphatidylserine, cardiolipin, phosphatidylethanolamine and phosphatidylcholine.

One example embodiment of the present invention is directed to a method for diagnosing, monitoring and/or staging Alzheimer's disease by conducting a blood test for redox-reactive autoantibodies (R-RAA). The autoantibodies can be autoantibodies that bind to phospholipid. The phospholipid can be, but not limited to, phosphatidylserine, cardiolipin, phosphatidylethanolamine, and phosphatidylcholine. The method of the present invention also comprises an assay that can detect antiphospholipid autoantibodies. The assay can be any assay known in the art that can detect antiphospholipid autoantibodies including, but not limited to, immunoassays. Some examples of an immunoassay can include, but not limited to radio immunoassay (RIA), enzyme immunoassay (EIA), flow cytometry, and Western blot. The autoantibodies that the assay of the present invention can detect include at least one of IgG, IgM, IgA, IgE, and IgD. The autoantibodies that the assay of the present invention can detect can bind to at least one phospholipid. The phospholipids can be, but not limited to, phosphatidylserine, cardiolipin, phosphatidylethanolamine and phosphatidylcholine.

Another example embodiment of the present invention is directed to a method for diagnosing, monitoring and/or staging neurological disorders in patients with cerebrovascular disease by conducting a blood test for redox-reactive autoantibodies (R-RAA). The autoantibodies can be autoantibodies that bind to phospholipid. The phospholipid can be, but not limited to, phosphatidylserine, cardiolipin, phosphatidylethanolamine, and phosphatidylcholine. The method of the present invention also comprises an assay that can detect antiphospholipid autoantibodies. The assay can be any assay known in the art that can detect antiphospholipid autoantibodies including, but not limited to, immunoassays. Some examples of an immunoassay can include, but not limited to radio immunoassay (RIA), enzyme immunoassay (EIA), flow cytometry, and Western blot. The autoantibodies that the assay of the present invention can detect include at least one of IgG, IgM, IgA, IgE, and IgD. The autoantibodies that the assay of the present invention can detect can bind to at least one phospholipid. The phospholipids can be, but not limited to, phosphatidylserine, cardiolipin, phosphatidylethanolamine and phosphatidylcholine.

The present invention is also directed to a blood test procedure for diagnosing, monitoring and/or staging neurological disorders which comprises an enzyme-linked immunosorbent assay comprising (1) a first diluent comprising an aqueous buffer containing bovine serum albumin and (2) a second diluent comprising an aqueous buffer containing adult bovine plasma, wherein the buffer containing the bovine serum albumin detects antiphospholipid autoantibodies which are independent of plasma-protein binding factors, and wherein the buffer containing the adult bovine plasma detects antiphospholipid autoantibodies which are dependent upon plasma-protein binding factors. The phospholipid can be phosphatidylserine, cardiolipin, phosphatidylethanolamine, and phosphatidylcholine. Neurological disorders can include, but not limited to, Parkinson's, Alzheimer's, multiple sclerosis (MS) that are associated with increased levels of oxidative stress in the CNS, as well as neurological disorders in patients with cerebrovascular disease. Again, different stages of a neurological disorder, such as Alzheimer's disease can be determined via the method of the present invention by amount of redox-reactive autoantibodies identified. The later the stage, the less amount of redox-reactive autoantibodies is present. Nearer to a much later stage, sometimes no redox-reactive autoantibodies are detectable.

Another embodiment of the present invention is directed to a blood test procedure for diagnosing, monitoring and/or Alzheimer's disease which comprises an enzyme-linked immunosorbent assay comprising (1) a first diluent comprising an aqueous buffer containing bovine serum albumin and (2) a second diluent comprising an aqueous buffer containing adult bovine plasma, wherein the bovine serum albumin buffer detects antiphospholipid autoantibodies which are independent of plasma-protein binding factors, and wherein the adult bovine plasma buffer detects antiphospholipid autoantibodies which are dependent upon plasma-protein binding factors. The phospholipid can be phosphatidylserine, cardiolipin, phosphatidylethanolamine, and phosphatidylcholine.

The present invention relates to the present invention relates to a kit for diagnosing, monitoring and/or staging neurological disorders which comprises an assay which can detect antiphospholipid autoantibodies. Neurological disorders can include, but not limited to, Parkinson's, Alzheimer's, multiple sclerosis (MS) that are associated with increased levels of oxidative stress in the CNS, as well as neurological disorders in patients with cerebrovascular disease.

Further, the present invention relates to a kit for diagnosing, monitoring and/or staging Alzheimer's disease which comprises an assay which can detect antiphospholipid autoantibodies. The autoantibodies are at least one of IgG, IgM, IgA, IgE, and IgD. The autoantibodies are autoantibodies which bind to phospholipids. The phospholipids can be, but not limited to, at least one of phosphatidylserine, cardiolipin, phosphatidylethanolamine and phosphatidylcholine. The assay can be any assay known in the art that can detect antiphospholipid autoantibodies including, but not limited to, immunoassays. Some examples of an immunoassay can include, but not limited to radio immunoassay (RIA), enzyme immunoassay (EIA), flow cytometry, and Western blot. The autoantibodies that the assay of the present invention can detect include at least one of IgG, IgM, IgA, IgE, and IgD. The autoantibodies that the assay of the present invention can detect can bind to at least one phospholipid. The phospholipids can be, but not limited to, phosphatidylserine, cardiolipin, phosphatidylethanolamine and phosphatidylcholine.

In addition, the present invention is directed to a biomarker for diagnosing, monitoring and/or staging neurological disorders comprising redox-reactive autoantibodies. The autoantibodies can be autoantibodies that bind to phospholipid. The phospholipid can be, but not limited to, phosphatidylserine, cardiolipin, phosphatidylethanolamine, or phosphatidylcholine. Neurological disorders can include all neurological disorders known in the art such as, but not limited to, Parkinson's, Alzheimer's, multiple sclerosis (MS) that are associated with increased levels of oxidative stress in the CNS. Neurological disorders can include, but are not limited to, neurological disorders in patients with cerebrovascular disease.

One other embodiment of the present invention is direct to a biomarker for diagnosing, monitoring and/or staging Alzheimer's disease comprising redox-reactive autoantibodies (R-RAA). Again, the autoantibodies can be autoantibodies that bind to phospholipids, and the phospholipid can be can be, but not limited to, phosphatidylserine, cardiolipin, phosphatidylethanolamine, and phosphatidylcholine.

The biomarker of the present invention detect specific antibodies within an individual that have the capability to act as autoimmune antibodies (antibodies that attack one's own tissues) once they are "unmasked" via reduction-oxidation (redox) reactions. Medical application of the technology of the present invention has the ability to revolutionize the diagnosis and treatment of a host of diseases. Through the technology of the present invention, redox-reactive autoantibodies (R-RAA) can be used as biomarkers to test for and potentially determine the staging of specific diseases, such as Alzheimer's disease and certain types of cancer. The biomarkers of the present invention provide opportunities for monitoring and validating potential therapeutic and drug applications during clinical trials.

The present inventor has demonstrated that that patients with Alzheimer's disease show a deficit in redox-reactive autoantibodies in both their spinal fluid and blood when compared with age-matched, putatively healthy individuals. Essentially, these autoantibodies appear significantly decreased and/or depleted in Alzheimer's patients, and the extent of autoantibody depletion may potentially help define the severity and progression of Alzheimer's disease for each patient.

The discovery of redox-reactive autoantibodies (R-RAA) originated after the present inventor learned of an experiment where antiphospholipid autoantibodies (aPL) were found in mice that had been injected with bacteria and/or viral particles. The present inventor performed clinical testing for the identification of aPL, which are normally associated with abnormal blood clotting. The present inventor tested blood samples in culture bottles from several patients with sepsis (massive bacterial infections), and found that aPL were present. The present inventor found, however, that control blood samples from non-septic patients when placed in culture bottles, also converted to aPL positive even though these non-septic patients did not have a bacterial infection. After numerous subsequent tests, the present inventor concluded that the aPL were being produced by the components of the blood culture bottle. The present inventor found that hemin, a physiological oxidizer, as well as other oxidizing agents, for example, potassium permanganate or electromotive force (EMF) was responsible for the unmasking of aPL in the blood samples of both the septic and non-septic individuals. Upon additional experimentation, the present inventor demonstrated that oxidation can both mask and unmask not just aPL, but many other autoantibodies as well. Further, the present inventor found that these redox-reactive autoantibodies are found in the blood, breast milk, and cerebrospinal fluid of humans and in the blood of a variety of mammalian and avian species.

The present inventor demonstrated that a new family of autoantibodies that are produced when they undergo an oxidation-reduction reaction, naming them as redox-reactive autoantibodies (R-RAA).

The present inventor also demonstrated that specific antibodies in the body have the capability to act as autoimmune antibodies (antibodies that attack one's own tissues) once they are "unmasked" via reduction-oxidation (redox) reactions. These antibodies display no autoantibody reactivity in their native state. However, in the laboratory, these antibodies can undergo a redox reaction wherein they lose an electron(s) to an oxidizing agent such as hemin. When this happens, the antibodies are "unmasked" to behave in vitro as autoantibodies associated with autoimmune disorders. This reaction can be reversed as well, where autoantibodies from individuals with autoimmune disease can be "masked" and no longer detected in diagnostic laboratory tests.

The redox-reactive autoantibodies of the present invention can be utilized in many medical fields beyond autoimmune disease as well. The present inventor has data demonstrating that redox-reactive autoantibodies can act as biomarkers to enable the improved understanding, diagnosis, and treatment of other neurodegenerative diseases such as Alzheimer's disease. In people with Alzheimer's disease (AD), changes in the brain may begin 10 to 30 years before any noticeable signs or symptoms appear. As a result, AD may not be diagnosed until many years after the disease process begins. The biomarker and method of the present invention can identify the disease in early stages. The present inventor found that in normal human cerebrospinal fluid (CSF), redox-reactive autoantibodies are detectable after redox exposure.

The present inventor found that oxidation reactions known to cause senile plaques and neurofibrillary tangles in AD patients' brains can also play a role in unmasking redox-reactive autoantibodies, which then cause them to bind to or target brain tissue. Hence, since the autoantibodies are binding to brain tissue upon oxidation, they cause the tissue to degenerate; thus they are no longer found in the CSF, and they become undetectable in laboratory tests after redox exposure.

The present invention can determine the severity and progression of AD for each patient. Similarly, the present invention has data demonstrating a decrease in redox-reactive autoantibodies in the blood of AD patients, thereby creating the possibility of offering a less invasive test to diagnose Alzheimer's disease.

Example 1

Blood Samples

Sixteen blood (serum) samples from Alzheimer's disease (AD) patients purchased from Eunoe, Inc. (Pleasanton, Calif.) and 17 normal age-matched volunteer blood donor serum samples purchased from the Central Indiana Regional Blood Center (Indianapolis, Ind.) were used for the study. The AD serum samples were collected from 11 females and 5 males with an average age of 75 (range 62-85). Volunteer blood donors consisted of females and males; average age was 72, (ranged 65-84). All samples were coded; individuals ages and dates of phlebotomy were provided but no personal identifiable information was included with the samples.

aPL ELISA

The detection of serum aPL before and after oxidation was assessed by using an in-house enzyme-linked immunosorbent assay (ELISA) that used two specimen diluents, one containing 1% bovine serum albumin (BSA) in TRIS-buffered saline (TBS) and the second diluent containing 10% adult bovine plasma (ABP) in TBS (McIntyre J A, Wagenknecht D R, Waxman D W. Frequency and specificities of antiphospholipid antibodies (aPL) in volunteer blood donors. Immunobiology 2003; 207:59-63, which is incorporated herein by its entirety). The BSA diluent allows detection of aPL that is independent of plasma-protein binding factors, whereas the ABP diluent detects aPL that is dependent upon the binding of a plasma proteins(s) to the phospholipids. The 4 aPL specificities assessed were phosphatidylserine (PS), cardiolipin (CL), phosphatidylethanolamine (PE) and phosphatidylcholine (PC). IgG, IgM and IgA isotypes were evaluated. In total, Alzheimer's disease patient samples were compared to normal age-matched sera in 24 independent tests.

Redox Optimization

The optimal dilution of the normal sera versus the final concentration of the oxidizing agent (hemin) was first determined by checkerboard analyses. A 1/10 dilution of serum showed optimal unmasking of aPL after addition of 22 µl of hemin (23 mM) per 1.0 ml of diluted serum and overnight incubation at 36 degrees in a rocking incubator. Serum dilution is required to counter the numerous components in the sera that can function as antioxidants.

Statistics

The non-parametric Mann-Whitney U-test was used for assessing whether two samples came from the same distribution. SPSS version 16 (Chicago, Ill.) was used for this analysis. As an exercise, the machine learning software known as Classification and Regression Trees, CART version 6.0, developed by Salford Systems, San Diego, Calif. (Steinberg D, Colla P. CART: Tree-structure non-parametric data analysis. San Diego, Calif.: Salford Systems; 1995), and based on Breinan's original algorithm (Breinan et al. Classification and regression trees. Pacific Grove, Calif.: Wadsworth Publishing Co; 1984), was used to crate an inductive decision tree to classify the sample patients. An inductive decision is a set of rules represented by decisional nodes and leaves (i.e., terminal nodes) that are assigned to a class.

The learning process consists of selecting the most discriminative variable according to an impurity function to partition the data, and repeating this partition recursively until the nodes are considered pure enough to be terminal and then pruning the resultant complete tree to avoid over fitting. Another technique was also investigated for classification, Fisher's linear discriminate analysis. Fisher's linear discriminant (Fisher R A. The use of multiple measurements in taxonomic problems. Ann Eugen 1936; 7:179-188) is a method used in statistics to find the linear combination of features which best separate two or more classes of objects (AD and Normal here) with the resulting combination used as a linear classifier. The present inventor noted that the models derived from either of the discriminant techniques at this juncture are in-sample models only.

Results

A natural occurring physiological concentration of a hemoglobin-like molecule (hemin) containing coordinated iron was used to oxidize the diluted serum samples. Hemin can participate in oxidation reduction reactions as can the selective enhancement of aromatic amino acids (tyrosine, tryptophan) found in an antibody's hypervariable antigen binding site, i.e., the complementarity determining region, (CDR) (McIntyre J A, Faulk W P. Redox-reactive autoantibodies: Biochemistry, characterization, and specificities. Clin Rev Allergy Immunol 2009, 37:49-54, which is incorporated herein by reference in its entirety). Overnight incubation of serum samples during exposure to hemin causes the unmasking of R-RAA. The results of aPL testing for the untreated normal sera versus AD sera and the hemin treated normal sera versus the AD sera are shown in Table 1 below.

TABLE 1

ELISA STUDIES OF ALZHEIMER'S VERSUS NORMAL, AGE-MATCHED SERA FOR ANTIPHOSPHOLIPID AUTOANTIBODY ACTIVITIES BEFORE AND AFTER OXIDATION WITH HEMIN

| | | Untreated Serum | | | Hemin Treated Serum | | |
|---|---|---|---|---|---|---|---|
| | | AD Mean (SD) | Normal Mean (SD) | p-value | AD Mean (SD) | Normal Mean (SD) | p-value |
| IgG PS | BSA | 0.025 (0.09) | 0.023 (0.055) | 0.444 | 0.230 (0.137) | 0.341 (0.157) | 0.058 |
| | ABP | 0.019 (0.036) | 0.034 (0.116) | 0.929 | 0.560 (0.171) | 0.670 (0.179) | 0.058 |
| IgG CL | BSA | 0.158 (0.247) | 0.152 (0.148) | 0.683 | 0.274 (0.156) | 0.285 (0.132) | 0.845 |
| | ABP | 0.062 (0.083) | 0.100 (0.143) | 0.127 | 0.636 (0.093) | 0.650 (0.139) | 0.444 |
| IgG PE | BSA | 0.027 (0.028) | 0.070 (0.037) | <=0.001 | 0.183 (0.053) | 0.305 (0.085) | <=0.001* |
| | ABP | 0.135 (0.142) | 0.099 (0.064) | 0.709 | 0.942 (0.934) | 0.969 (0.141) | 0.191 |
| IgG PC | BSA | 0.062 (0.046) | 0.109 (0.061) | 0.005 | 0.640 (0.148) | 0.776 (0.131) | 0.009* |
| | ABP | 0.058 (0.054) | 0.062 (0.059) | 0.709 | 0.398 (0.109) | 0.390 (0.100) | 0.790 |
| IgA PS | BSA | 0.016 (0.013) | 0.006 (0.008) | 0.014 | 0.147 (0.093) | 0.151 (0.107) | 0.873 |
| | ABP | 0.027 (0.045) | 0.007 (0.008) | 0.037 | 0.418 (0.248) | 0.286 (0.118) | 0.146 |
| IgA CL | BSA | 0.064 (0.189) | 0.007 (0.007) | 0.309 | 0.107 (0.147) | 0.151 (0.107) | 0.657 |
| | ABP | 0.023 (0.045) | 0.006 (0.008) | 0.929 | 0.311 (0.093) | 0.286 (0.118) | 0.136 |
| IgA PE | BSA | 0.030 (0.021) | 0.059 (0.030) | 0.008 | 0.100 (0.035) | 0.134 (0.063) | 0.217 |
| | ABP | 0.037 (0.034) | 0.027 (0.038) | 0.118 | 0.582 (0.162) | 0.567 (0.217) | 0.845 |
| IgA PC | BSA | 0.040 (0.022) | 0.040 (0.025) | 0.709 | 0.183 (0.085) | 0.179 (0.082) | 0.958 |
| | ABP | 0.014 (0.015) | 0.013 (0.005) | 0.657 | 0.075 (0.040) | 0.061 (0.024) | 0.362 |
| IgM PS | BSA | 0.005 (0.010) | 0.008 (0.024) | 0.683 | 0.009 (0.009) | 0.019 (0.018) | 0.081 |
| | ABP | 0.006 (0.008) | 0.004 (0.014) | 0.102 | 0.072 (0.054) | 0.122 (0.074) | 0.028 |
| IgM CL | BSA | 0.007 (0.019) | 0.008 (0.018) | 0.606 | 0.020 (0.017) | 0.032 (0.039) | 0.557 |
| | ABP | 0.009 (0.019) | 0.015 (0.020) | 0.657 | 0.159 (0.092) | 0.243 (0.146) | 0.053 |
| IgM PE | BSA | 0.009 (0.018) | 0.011 (0.020) | 0.581 | 0.030 (0.041) | 0.046 (0.034) | 0.019 |
| | ABP | 0.029 (0.059) | 0.026 (0.034) | 0.510 | 0.233 (0.104) | 0.483 (0.307) | 0.003* |
| IgM PC | BSA | 0.015 (0.019) | 0.026 (0.032) | 0.068 | 0.063 (0.040) | 0.097 (0.060) | 0.068 |
| | ABP | 0.020 (0.018) | 0.020 (0.017) | 0.817 | 0.032 (0.019) | 0.056 (0.036) | 0.045 | p-values from Mann-Whitney U tests, exact significance [2 * 1-tailed test], Not corrected for ties.
*denotes the mean ELISA OD values for the aPL specificity exceeds the established cutoff as determined after testing 750 normal blood volunteer donors.

As shown in Table 1 above, of the 48 comparisons made between the AD and normal serum samples, 11 showed statically significant (p<0.05) differences. In 9 of the 11 differences detected, the mean optical density (OD) readings for aPL ELISA values were lower among the AD patients sera. Two of 11 OD values were higher in the AD group; however, these were observed in the non-treated sample comparisons between the AD and normals. Because many mean values were below the positive/negative cut-off established for this assay, the relevance of these variances is not definite.

In contrast, 3 of the 6 aPL mean values between the AD and normal serum samples in the hemin-treated group were above the positive/negative thresholds established for these aPL specificities. Two of these 3 predictor variable are IgG aPE in BSA buffer, and IgM aPE in ABP buffer. The mean OD values observed for these aPL specificities were subjected to a statistical CART (Classification And Regression Tree) analysis, which following computational differences of aPL levels in these 33 individuals, reached a level of 84% sensitivity and 100% specificity for predicting stratification of the Alzheimer's group versus the normal blood donor group (FIG. 1). A simple rule based classifier derived from this CART analysis would be: Either an OD value of hemin treated IgG PE BSA greater than 0.28 or an OD value of hemin treated IgG PE BSA less than 0.28 combined with an OD value of hemin treated IgM PE ABP less than 0.13 indicates a non AD patient. A second statistical approach used was the Fisher's Linear Discriminant Analysis, wherein the specificity is calculated to be 94% and the sensitivity is 88%. The Fisher's discriminant function for classifying the AD and normal patient is:

$$X = 11.362 \, (OD \text{ value hemin treated } IgG \, PE \, BSA) + $$
$$0.652 \, (OD \text{ value hemin treated } IgG \, PC \, BSA) + $$
$$2.211 \, (OD \text{ value hemin treated } IgM \, PE \, ABP) - 4.051$$

with positive values resolving to normal patients and negative values resolving to AD patients. The discriminant group centroids are 0.984 and −1.046, respectively.

Figure 2:
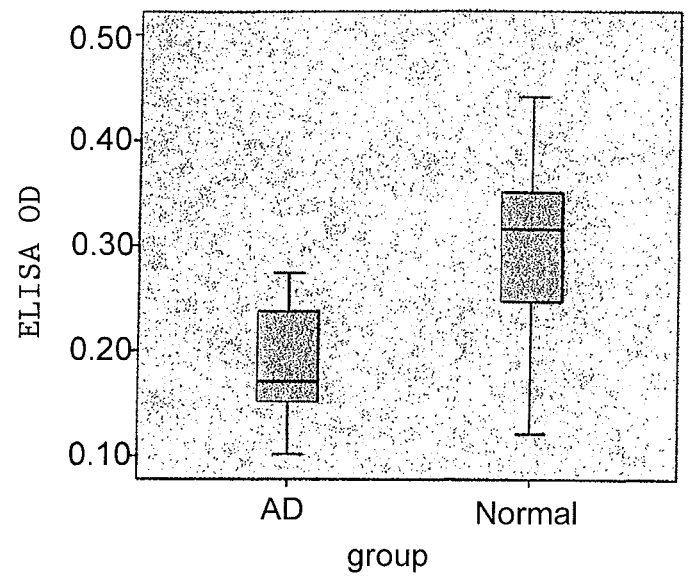
FIG. 2 shows vertical Scatter Box Plots illustrating an alternative statistical expression of the significant data resulting from the analyses of Table 1. The median is identified by the line inside the box. The length of the box represents the interquartile range (IQR) computed from Tukey's hinges. The ends of the box are the first and third quartiles end values. Values more than 3 IQR's from the end of the box are denoted with an asterisk (*). Values more than 1.5 IQR's are labeled as outliers (o).
Figure 2:
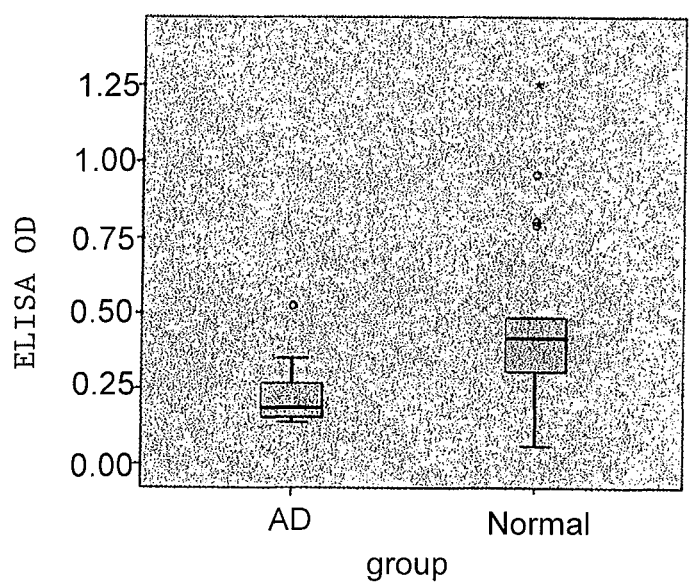

An alternative mathematical expression of the significant data resulting from the analyses of Table 1 is shown in FIG. 2 as vertical box plots. Scatter box plots provide a quick visual reference to observe the relative differences in R-RAA between the normal individuals versus the AD patients.

Example 2

Table 2 below illustrates results of a PL testing for untreated normal sera versus AD sera and hemin treated normal sera versus the AD sera. The PL test was conducted as recited in example 1. These data represent an out-of-sample analysis for testing.

TABLE 2

Sorted by IgM_PE10%

| Sample ID | IgG_PE 1%_mean | IgM_PE 10%_mean | New Assignments |
|---|---|---|---|
| 202255 | 0.037 | 0.054 | I |
| 202653 | 0.055 | 0.054 | I |
| 207543 | 0.042 | 0.055 | I |
| 211230 | 0.247 | 0.060 | N |
| 202170 | 0.294 | 0.080 | N |
| 207570 | 0.169 | 0.082 | I |
| 207505 | 0.089 | 0.091 | AD |
| 202679 | 0.118 | 0.100 | I |
| 207382 | 0.247 | 0.118 | N |
| 207400 | 0.184 | 0.121 | N |
| 207004 | 0.153 | 0.157 | N |
| 202680 | 0.081 | 0.188 | AD |
| 207508 | 0.114 | 0.206 | AD |
| 207436 | 0.127 | 0.218 | AD |
| 207539 | 0.222 | 0.267 | N |
| 207512 | 0.160 | 0.290 | I |
| 202317 | 0.130 | 0.309 | AD |
| 202735 | 0.144 | 0.633 | AD |
| new ad | 0.114029422 | 0.274217793 | |
| new I | 0.096901997 | 0.105736213 | |
| new n | 0.224389547 | 0.133746586 | |

AD = Alzheimer's
N = Normals
I = MCI (mild cognitive impairment)

The purpose of the above description and examples is to illustrate some embodiments of the present invention without implying any limitation. It will be apparent to those of skill in the art that various modifications and variations may be made to the kit and method of the present invention without departing from the spirit or scope of the invention. All publications cited herein are incorporated by references in their entireties.

I claim:

1. A method for diagnosing, monitoring and/or staging Alzheimer's disease which comprises:
   providing a blood sample from a human subject;
   oxidizing the blood sample from a human subject in vitro; and then
   conducting a blood test for determining a level of at least one redox-reactive autoantibody in the blood sample;
   comparing the level of the at least one redox-reactive autoantibody to a predetermined value; and
   diagnosing, monitoring and/or staging Alzheimer's disease based on the comparison between the level of the at least one redox-reactive autoantibody and the predetermined value.

2. A method in accordance with claim 1 wherein the at least one autoantibody is at least one of IgG, IgM, IgA, IgE, and IgD.

3. A method in accordance with claim 1 wherein the at least one autoantibody comprises autoantibodies which bind to phospholipids.

4. A method in accordance with claim 3 wherein the phospholipids are at least one of phosphatidylserine, cardiolipin, phosphatidylethanolamine and phosphatidylcholine.

5. A method according to claim 1 wherein the blood test comprises an assay that can detect antiphospholipid autoantibodies.

6. A method in accordance with claim 5 wherein the at least one autoantibody is at least one of IgG, IgM, IgA, IgE, and IgD.

7. A method in accordance with claim 5 wherein the at least one autoantibody comprises autoantibodies that bind to at least one of phosphatidylserine, cardiolipin, phosphatidylethanolamine and phosphatidylcholine.

8. A method in accordance with claim 1, wherein the blood sample is a diluted blood sample.

9. A method in accordance with claim 8, wherein the at least one autoantibody is at least one of IgG, IgM, IgA, IgE, and IgD.

10. A method in accordance with claim 8, wherein the at least one autoantibody comprises autoantibodies that bind to at least one of phosphatidylserine, cardiolipin, phosphatidylethanolamine and phosphatidylcholine.

11. A method in accordance with claim 1, wherein oxidizing the blood sample from a human subject in vitro comprises oxidizing the blood sample with an oxidizing agent in vitro.

12. A method in accordance with claim 11, wherein the oxidizing agent is hemin.

13. A method for treating Alzheimer's disease which comprises:
- providing a blood sample from a human subject;
- oxidizing the blood sample from a human subject in vitro; and then
- conducting a blood test for determining a level of at least one redox-reactive autoantibody in the blood sample;
- comparing the level of the at least one redox-reactive autoantibody to a predetermined value;
- diagnosing, monitoring and/or staging Alzheimer's disease based on the comparison between the level of the at least one redox-reactive autoantibody and the predetermined value; and
- when the patient is diagnosed with Alzheimer's disease, treating the human subject based on the diagnosing, monitoring and/or staging.

* * * * *